United States Patent [19]
Hutchins

[11] Patent Number: 5,442,970
[45] Date of Patent: Aug. 22, 1995

[54] WATER SAMPLING DEVICE

[76] Inventor: Charles D. Hutchins, 212 Dogwood Lane, Belmont, N.C. 28012

[21] Appl. No.: 264,605
[22] Filed: Jun. 23, 1994
[51] Int. Cl.⁶ ............................................. G01N 1/12
[52] U.S. Cl. ............................................. 73/864.63
[58] Field of Search .......... 73/863.03, 864.34, 864.51, 73/864.59, 864.63–864.67, 864.73; 220/752, 755, 757, 769; 16/114, 114 A, 115

[56] References Cited

U.S. PATENT DOCUMENTS

| | | | |
|---|---|---|---|
| 41,652 | 2/1864 | Terneson | 220/757 |
| 643,492 | 2/1900 | Fromholz | 16/114 A |
| 2,497,384 | 2/1950 | Young | 16/114 A |
| 2,501,940 | 3/1950 | Hibbard | 16/114 A |
| 2,624,201 | 12/1953 | Thomson . | |
| 2,660,457 | 11/1953 | Mallon | 16/115 |
| 3,329,308 | 7/1967 | Pool . | |
| 3,686,949 | 8/1972 | Hackett . | |
| 3,692,490 | 9/1972 | Hall . | |
| 3,960,021 | 6/1976 | Jones . | |
| 4,061,038 | 12/1977 | Clarke, Jr. . | |
| 4,112,769 | 9/1978 | Falk . | |
| 4,346,613 | 8/1982 | Turner et al. . | |
| 4,453,424 | 6/1984 | Hackett | 73/864.59 |
| 4,454,775 | 6/1984 | Ellis . | |
| 4,563,896 | 1/1986 | Arnold | 73/864.51 |
| 4,659,125 | 4/1987 | Chuan | 16/115 |
| 4,754,656 | 7/1988 | Charm | 73/864.63 |
| 4,979,402 | 12/1990 | Ryan et al. | 73/864.51 |
| 4,982,615 | 1/1991 | Sultan et al. | 73/864.51 |
| 4,998,000 | 3/1991 | Halloran | 16/114 A |
| 5,202,094 | 4/1993 | Jones et al. | 16/114 R |

FOREIGN PATENT DOCUMENTS 1018829  2/1966  United Kingdom ............. 73/864.51

Primary Examiner—Robert Raevis
Attorney, Agent, or Firm—Bell, Seltzer, Park & Gibson

[57] ABSTRACT

A sampling device for selecting a sample of water from a body of polluted water is disclosed. The sampling device includes a telescopically extendable elongated pole having a handle at a large end and a retaining member at a small end for connecting a sample receptacle thereto. The sample receptacle is open at the top and has a support member formed integral with and extending laterally from a side of the receptacle. The support member is adapted to connect the sample receptacle to the retaining member.

2 Claims, 2 Drawing Sheets

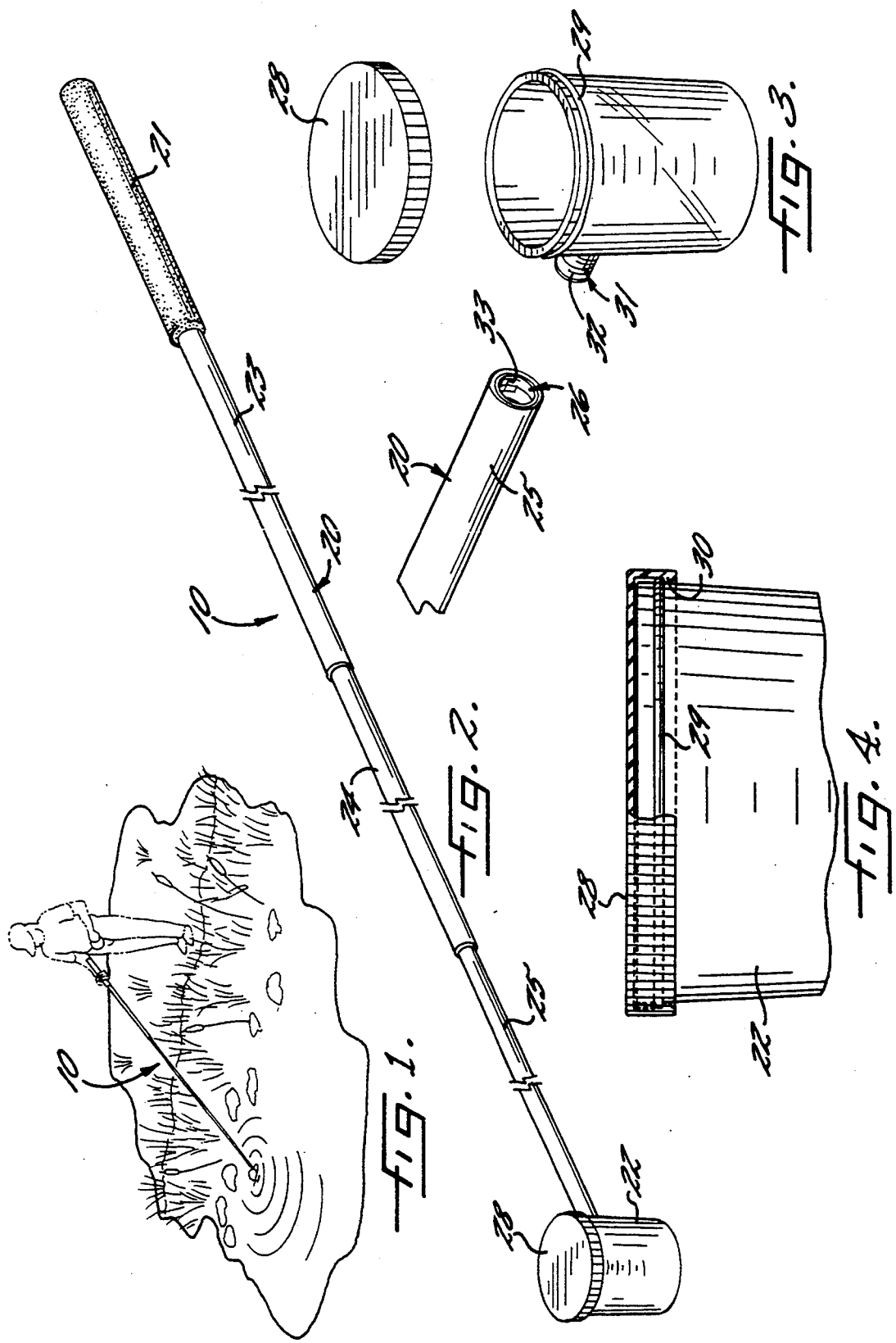

WATER SAMPLING DEVICE

BACKGROUND OF THE INVENTION (1) Field of the Invention

The present invention relates to an improved water sampling device. More particularly, the present invention relates to a water sampling device having a sample receptacle connected to an elongated telescopically extendable pole.

(2) Description of the Prior Art

One of the steps to be taken in determining the pollution in a given body of water is to periodically take samples therefrom. Quite frequently the area where the polluted sample needs to be taken is not directly adjacent to the shore making sampling difficult. Since the sampling areas of the body of water are not always easily accessible, it is difficult at times to obtain a true sample of the polluted water without time consuming spillage or having to use a boat.

When testing water for pollutants and the like it is necessary for a laboratory technician to first obtain a suitable sample. Many technicians use a string and bottle device which is unsatisfactory for efficient and accurate testing. The string and bottle device can be difficult to use and requires that the technician be able to stand relatively close to the water's edge to obtain samples more than a short distance from the shore. When samples are obtained using this technique the bottle is tossed in the general direction that the sample is to be taken and the string is pulled toward the technician to retrieve the bottle containing the sample. The water sample is then poured from the bottle into another container and the string and bottle arrangement is used to obtain another sample. When using this technique, there is an inherent chance that subsequent samples from different testing sites will be contaminated if the technician fails to properly rinse the bottle after obtaining the first sample.

Other devices for obtaining samples of polluted water are likewise known. For example, in Clarke, U.S. Pat. No. 4,061,038, there is disclosed a mosquito larvae dipper which includes a cup having a handle. The cup has generally diametrically opposed pouring grooves for emptying each sample into another container for analysis. The device has a handle support formed integrally with the cup wall which extends upwardly from the wall and has a coaxially arranged cylindrical opening for mounting the handle. This device, like the string and bottle, requires that the sample be poured into another container before transportation to the laboratory.

The device of the present invention overcomes the difficulties associated with the prior art devices described above by providing a water sampling device for easily obtaining a number of uncontaminated samples of polluted water at a distance away from the shore of a body of water.

SUMMARY OF THE INVENTION

It is therefore an object of the present invention to provide a simple, easy to use device for obtaining a water sample at some distance from the edge of a body of water.

Another object of the present invention is to provide a sampling receptacle connected to an extendable pole in which the sampling receptacle is easily removed from the pole and other receptacle connected thereto for taking another sample.

Yet another object of the present invention is to provide a water sampling device in which the laboratory technician can conveniently obtain uncontaminated samples.

The objects of the invention are accomplished by providing a manually operated sampling device for selecting a sample of water from a body of polluted water. The sampling device includes a lightweight telescopically extending elongate pole member and a sample receptacle connected to the elongated pole.

The telescopically extendable elongated pole member has a large end and a small end. The large end has a handle and the small end has a retaining member for gripping engagement of a sample receptacle. The sample receptacle is preferably of annular construction having an open top for receiving the polluted water sample. The receptacle has a support member formed integral with and extending laterally from a side thereof. The support member is connected to the retaining member at the small end of the elongated pole. The receptacle may be provided with a removable lid for securing the sample in an uncontaminated condition prior to analysis. The lid is preferably of the snap-on type but may be of any convenient type, such as a screw-on cap. It should be understood that the sample receptacle may be of various sizes depending upon the water analysis to be made.

As noted, the receptacle is connected to the elongated pole. The connection of the sample receptacle to the elongated pole may be through a variety of ways so long as the sample receptacle is easily and conveniently removable from the elongated pole so that another sample receptacle may be connected. In one embodiment the small end of the elongated pole has a plug with internal threads sized to co-operate with external threads on the receptacle support member inserted in its open end. In another embodiment the receptacle support member includes a biasing means which biases a pair of lugs through holes in the retaining member wall and through mating holes in the small end of the elongated pole to form a quick release a fit for easily connecting the sample receptacle to the elongate pole.

Other objects, features and advantages of the present invention will become apparent from the following detailed description taken in conjunction with the accompanying drawings.

BRIEF DESCRIPTION OF THE DRAWINGS

FIG. 1 is an environmental view showing the sampling device of the present invention in use;

FIG. 2 is a perspective view of the sampling device of the present invention;

FIG. 3 is a perspective view showing the sampling receptacle of the present invention separated from the elongated pole;

FIG. 4 is a side view of the lid taken along line 3—3 of FIG. 3;

DETAILED DESCRIPTION OF PREFERRED EMBODIMENTS

Figure 5:
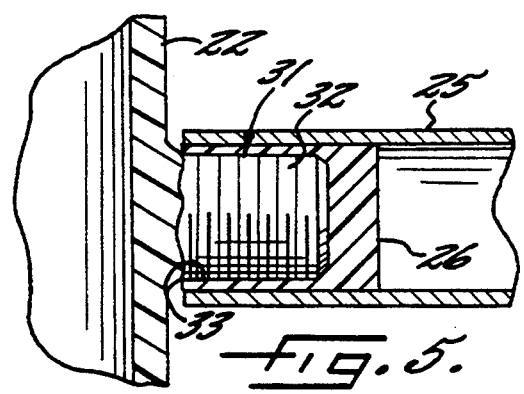
FIG. 5 is an exploded sectional view illustrating an embodiment of the sampling receptacle connected to the elongated pole.

Referring now to FIG. 1 there is shown an environmental view of the sampling device of the present invention in which the device, generally designated by 10, is used to obtain water samples from polluted bodies of water. The structure shown, i.e., having a telescopically extending pole and a sampling receptacle connected thereto, allows samples to be taken at a distance from the edge of a body of water.

As shown in FIG. 2, the water sampling device 10 includes a manually operated elongated telescopically extendable pole member 20 having a handle 21 at the large and end a small end for gripping engagement of a sampling receptacle 22. The telescopically extendable elongated pole member 20 has sections 23, 24, 25 of decreasing diameter allowing the pole to extend outwardly from a retracted 3–4 feet to an extended 12–16 feet depending upon the distance from the shore that the sample is to be taken. The section at the small end, shown in FIG. 2 as section 25, is typically hollow. The elongated pole is preferably made of a light weight extruded metal.

As shown in FIG. 3, sample receptacle 22 is an open top structure suitable for collecting water samples. The sample receptacle 22 may be of any suitable shape but is preferably of annular construction. The receptacle 22 is provided with a support member 31 formed integral with and extending laterally from a side of the receptacle for attachment to the small end 25 of elongated pole 20. In addition, the receptacle is provided with a rib 29 closely adjacent to and encircling the upper end of the sample receptacle 22 and a closure means, such as a lid 28, adapted to be secured over the rib by engaging flange 30 to form a snap-on fit, as shown in FIG. 4. Of course, it should be readily understood that other suitable means of securing a lid to the receptacle, such a screw-on top, during transportation to the laboratory for analysis may be used. The receptacle structure including the sample receptacle itself and the support means may be formed of a suitable plastic, for example, high impact polyethylene. Preferably the sample receptacle may be molded in a single operation by any one of a number of commercially available molding machines.

The sample receptacle 22 may be connected to the small end 25 of elongated pole 20 through a variety of ways so long as the receptacle is easily removable from the elongated pole so that another sample receptacle may be connected thereto. In the embodiment shown in FIG. 5 the small end 25 of the elongated pole 20 has a plug 26 inserted into the hollow end. The plug 26 has internal threads 33. The laterally extending support member 31 has external threads 32 that are sized to co-operate with the threads of plug 26.

Figure 6:
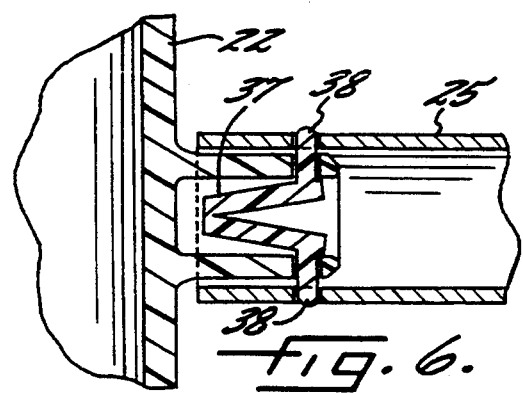
FIG. 6 is an exploded sectional view illustrating another embodiment of the sampling receptacle connected to the elongated pole.

In another embodiment, shown in FIG. 6, the receptacle support member 31 has a hollow recess in the lateral extension wherein is located a biasing means 37. The biasing means, as shown, has a pair of legs 36 extending in a V-shape having a pair of lugs 38 at the end of each leg. The biasing means is formed in such manner that the legs exert an outward force urging the lugs 38 through holes in the walls of said support member and mate with holes in the retaining member 25 whereby the sample receptacle may be easily connected to and detached from the elongated pole.

In use, the technician simply attaches the sample container to the elongated handle to obtain a suitable volume of pollutant from a body of water. Once the sample is retrieved, the cap is placed on the sample receptacle and the receptacle removed from the handle and a new sample receptacle is connected to the handle for obtaining another sample.

It will be noted by the present arrangement that the sample receptacle may be in any number of sizes depending upon the size sample desired, for example, 4 ounces to 16 ounces.

While the present invention has been described in connection with the exemplary embodiments thereof, it will be understood that any modifications will be apparent to those of ordinary skill in the art and that this application is intended to cover any adaptations or variations thereof. Therefore, it is manifestly intended that this invention be only limited by the claims and equivalents thereof.

What is claimed is:

1. A manually operated sampling device for taking a sample of water from a body of water, which comprises:

an elongated telescopically extendable pole member having a large end and a small end and having a handle at said large end and a retaining member at said small end for removably attachable engagement of a sample receptacle; and an open top sample receptacle capable of receiving a closure means having a support member integral with and extending laterally from a side thereof, said support member connected to said retaining member at said small end of said elongated pole for mounting said sample receptacle thereto so as to permit the use of said extendable pole member in obtaining samples of water at a predetermined distance from the shore of a body of water;

said support member comprises a biasing member having a pair of lugs at the end of legs extending through holes in the walls of said support member and mating with holes in said retaining member whereby said sample receptacle may be easily connected to and detached from said elongated pole.

2. The device according to claim 1 wherein said support member comprises said sample receptacle is of annular construction having a rib closely adjacent to and encircling the upper end of said sample receptacle and a closure adapted to be secured over said rib.

* * * * *